(12) United States Patent
Douglas-Hamilton

(10) Patent No.: US 6,675,605 B2
(45) Date of Patent: Jan. 13, 2004

(54) METHOD AND DEVICE FOR TRANSPORTING EQUINE SEMEN

(75) Inventor: Diarmaid H. Douglas-Hamilton, Beverly, MA (US)

(73) Assignee: Benbow Corporation, South Hamilton, MA (US)

( * ) Notice: Subject to any disclaimer, the term of this patent is extended or adjusted under 35 U.S.C. 154(b) by 0 days.

(21) Appl. No.: 10/268,299

(22) Filed: Oct. 10, 2002

(65) Prior Publication Data

US 2003/0084680 A1 May 8, 2003

Related U.S. Application Data

(60) Provisional application No. 60/328,528, filed on Oct. 10, 2001.

(51) Int. Cl.[7] ................................................. F25B 3/08
(52) U.S. Cl. ........................................ 62/457.2; 62/371
(58) Field of Search ............................. 62/457.1, 457.2, 62/371, 457.9

(56) References Cited

U.S. PATENT DOCUMENTS

| | | | |
|---|---|---|---|
| 4,134,359 A | 1/1979 | Redpath | 116/219 |
| 4,227,381 A | 10/1980 | Sullivan et al. | 62/223 |
| 4,530,816 A * | 7/1985 | Douglas-Hamilton | 422/1 |
| 5,030,200 A | 7/1991 | Judy et al. | 604/5 |
| 5,355,684 A * | 10/1994 | Guice | 62/54.2 |
| 5,735,401 A | 4/1998 | Cassou et al. | 206/469 |
| 5,899,088 A | 5/1999 | Purdum | 62/371 |
| 5,899,848 A | 5/1999 | Haubrich | 600/35 |
| 5,983,661 A | 11/1999 | Wiesman | 62/457.1 |
| 6,044,618 A | 4/2000 | Cassou et al. | 53/284 |
| 6,079,184 A | 6/2000 | Cassou et al. | 53/412 |
| 6,090,088 A | 7/2000 | Nichols | 604/347 |
| 6,149,579 A | 11/2000 | Lee | 600/35 |
| 6,230,515 B1 * | 5/2001 | Wiesman | 62/457.1 |
| 6,405,556 B1 * | 6/2002 | Bucholz | 62/457.2 |
| 2003/0084679 A1 * | 5/2003 | Charlton et al. | 62/371 |

* cited by examiner

*Primary Examiner*—Melvin Jones
(74) *Attorney, Agent, or Firm*—Lahive & Cockfield, LLP

(57) ABSTRACT

A container for storing and transporting semen, e.g., equine semen, along with a corresponding method of packing the container, is provided. The container is formed of an insulated box and an insulated cover. The insulated box and insulated cover each includes a collection of ridges and recesses to create a friction fit between the two that will only work with the insulated cover being placed on the insulated box in a predetermined orientation. A cooling pack is disposed on a floor of the insulated box. An insert is disposed to rest on the cooling pack inside the insulated box, such that the cooling pack is beneath the insert when the insulated box is in an upright position. The insert has at least one chamber for receiving a storage capsule holding the semen sample. The insulated cover frictionally fits on the insulated box and makes contact with the insert to hold the insert in place. The insert makes sufficient contact with the cooling pack to enable conductive cooling of the semen sample in the insert, regardless of orientation of the container. The materials forming the container are sufficiently inexpensive to consider the container disposable.

32 Claims, 4 Drawing Sheets ical Application No. 60/328,528, filed Oct. 10, 2001,
METHOD AND DEVICE FOR TRANSPORTING EQUINE SEMEN

RELATED APPLICATION

This application claims priority to, and the benefit of, U.S. Provisional Application No. 60/328,528, filed Oct. 10, 2001, now abandoned for all subject matter common to both applications. The disclosure of said provisional application is hereby incorporated by reference in its entirety.

FIELD OF THE INVENTION

The present invention relates to a method and device suitable for storing and transporting animal semen, and more particularly to a method and disposable device for storing and transporting equine semen.

BACKGROUND OF THE INVENTION

A device for transporting equine and other animal semen was introduced to the equine breeding market in 1984 with the trade name "The Equitainer" (at least a partial description of which can be found in U.S. Pat. No. 4,530,816). Since that time, horse breeding by artificial insemination using transported chilled semen has become dominant in the equine breeding sector. The technique of slowly cooling the sample en route to its destination has been an important contribution.

The Equitainer is carefully engineered to give a repeatable and reliable cooling rate and final temperature that is substantially independent of external conditions. Although the performance of the Equitainer is good, the structure is relatively bulky and not inexpensive to produce. The cost of the Equitainer implies that the container must be returned to the shipper after use. In many cases, this can be inconvenient.

The conventional Equitainer achieves a required cooling rate by placing a sample in a conductive cavity, known as the Isothermalizer, and interposing a barrier between the sample and the coolant. This configuration determines the rate at which heat can be transferred between the coolant and the sample. The volume of the sample is then adjusted using thermal ballast, to result in a desired controlled cooling rate. The sample and coolant assembly is packaged inside a large insulated cylindrical container, and dispatched to the user. There is an initial cooling rate when the start temperature is at about 37° C. of close to −0.3° C./minute. The cooling continues slowly en route, down to a minimum temperature typically 6° C., depending on exterior conditions.

It has been shown and reported in the industry that the best results are obtained for horse semen fertility when the cooling rate at 20° C. is in the vicinity of −0.1° C./min. This is to avoid a high rate of change to the cell temperature at the temperature where the lipid cell membranes are changing phase. The low temperature rate of change likely allows the proteins in the cell surface time to crystallize in an orderly fashion and avoid cell damage. The Equitainer design was based on this finding.

In addition to the Equitainer, a number of other conventional devices use a process of convection to cool the sample contained within the device. With convection, cooled air transfers heat from the sample to the coolant. The sample is normally transported in syringes ready for insemination, and a thermal barrier is introduced between the coolant and the sample to adjust cooling rate. The thermal barrier used is typically a Styrofoam sheet with one or more notches cut out. The Styrofoam sheet is placed between coolant block and sample, so that air can flow through the notches as it convects. The coolant block is normally placed above the sample. Cool air then falls through the holes in the Styrofoam and cools the sample. The sample is placed in a foamed plastic box, next to the Styrofoam thermal barrier and the coolant block.

The convection system does not independently control cooling rate and final temperature. In addition, the convection system is sensitive to orientation. This is evidenced by the fact that the cooling rate is about twice as fast when the system is upright verses when it is inverted, representing the difference between air convection cooling and air conduction cooling. To make a system in which the cooling rate is independent of orientation, convective cooling cannot be used. The failure to maintain a uniformly controlled cooling rate can have negative effects on the success rates of equine insemination.

SUMMARY OF THE INVENTION

There is a need in the art for a disposable container with similar reliable cooling rate properties as the Equitainer, but with the added constraint that the materials and components required must not only produce accurate and repeatable results, but must be simple, disposable, and inexpensive. The present invention is directed toward further solutions to address this need.

In accordance with one embodiment of the present invention, a storage and transportation container for storing and transporting a semen sample is provided. The container includes an insulated box having at least a first portion being a box protruding ridge, at least a second portion being a box recessed groove, and a floor. An insulated cover is provided having at least a first portion having a cover recessed groove and being located to receive the box protruding ridge only when the insulated cover is placed on the insulated box in a predetermined orientation. The insulated cover also has at least a second portion having a cover protruding ridge and being located to be received into the box recessed groove only when the insulated cover is placed on the insulated box in the predetermined orientation. A cooling pack is disposed on the floor of the insulated box. An insert is disposed to rest on the cooling pack inside the insulated box, such that the cooling pack is beneath the insert when the insulated box is in an upright position. The insert has at least one chamber for receiving a storage capsule holding the semen sample. The insulated cover frictionally fits on the insulated box and makes contact with the insert to hold the insert in place. The insert makes sufficient contact with the cooling pack to enable conductive cooling of the semen sample in the insert.

In accordance with various aspects of the present invention, the insulated box and the insulated cover are formed of foam plastic, such as Styrofoam, or the like. Likewise, the insert can also be made of foamed plastic, such as polyethylene, or the like. The choice of material rests on insulation properties and relative cost.

In accordance with further aspects of the present invention, the at least one chamber is sized and dimensioned to hold a storage capsule suitable for holding the semen sample. The semen sample is equine semen. The storage capsule is at least one of a syringe and a tube.

The storage capsule can be sized and dimensioned differently, and can include sizes with volume capacities of 20 ml or 50 ml. The relative size of the storage capsule will affect the number of chambers required in the insert to hold the storage capsules. Since the total amount of material to be cooled will affect the cooling rate, thermal ballast can be added to the storage capsule, if necessary, to keep the total volume in the range of 80 ml to 120 ml in one example embodiment. The thermal ballast is typically water, contained in a suitable tube, initially at substantially the same temperature as the semen sample. Smaller capsules would result in more capsules being required and thus a plurality of chambers required in the insert. A sum of the capacity of the semen sample and the thermal ballast able to be stored in the at least one chamber according to one embodiment is about 90 ml to about 110 ml, or about 80 ml to about 120 ml. With such a semen sample quantity, a cooling rate of the semen sample in the insert is about 0.1° C./min at about 20° C.

In accordance with further aspects of the present invention a method of packing a semen sample for storage or transportation includes providing an insulated box having a floor. A cooling pack is placed on the floor of the insulated box. An insert is placed on top of and substantially in contact with the cooling pack, the insert having at least one storage capsule holding the semen sample disposed within at least one chamber of the insert. An insulated cover is placed on top of and in contact with the insert, the insulated cover having a friction fit with the insulated box.

BRIEF DESCRIPTION OF THE DRAWINGS

The present invention will become better understood with reference to the following description and accompanying drawings, wherein.

DETAILED DESCRIPTION

Figure 1A:
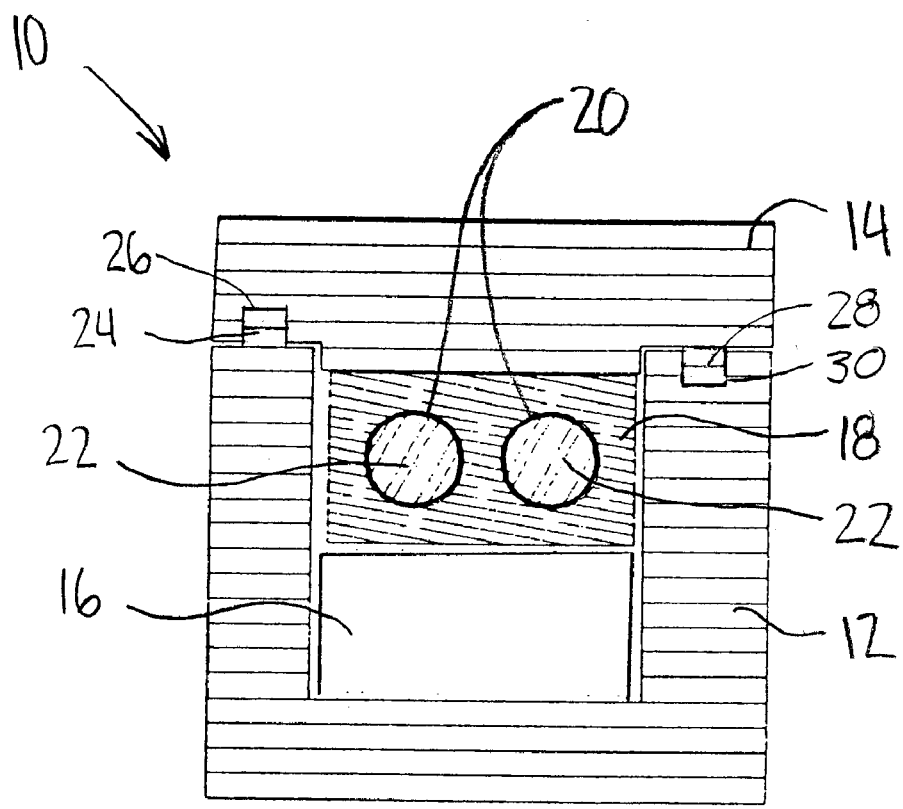
FIG. 1A is a front view of a disposable container, according to one aspect of the present invention.
Figure 1B:
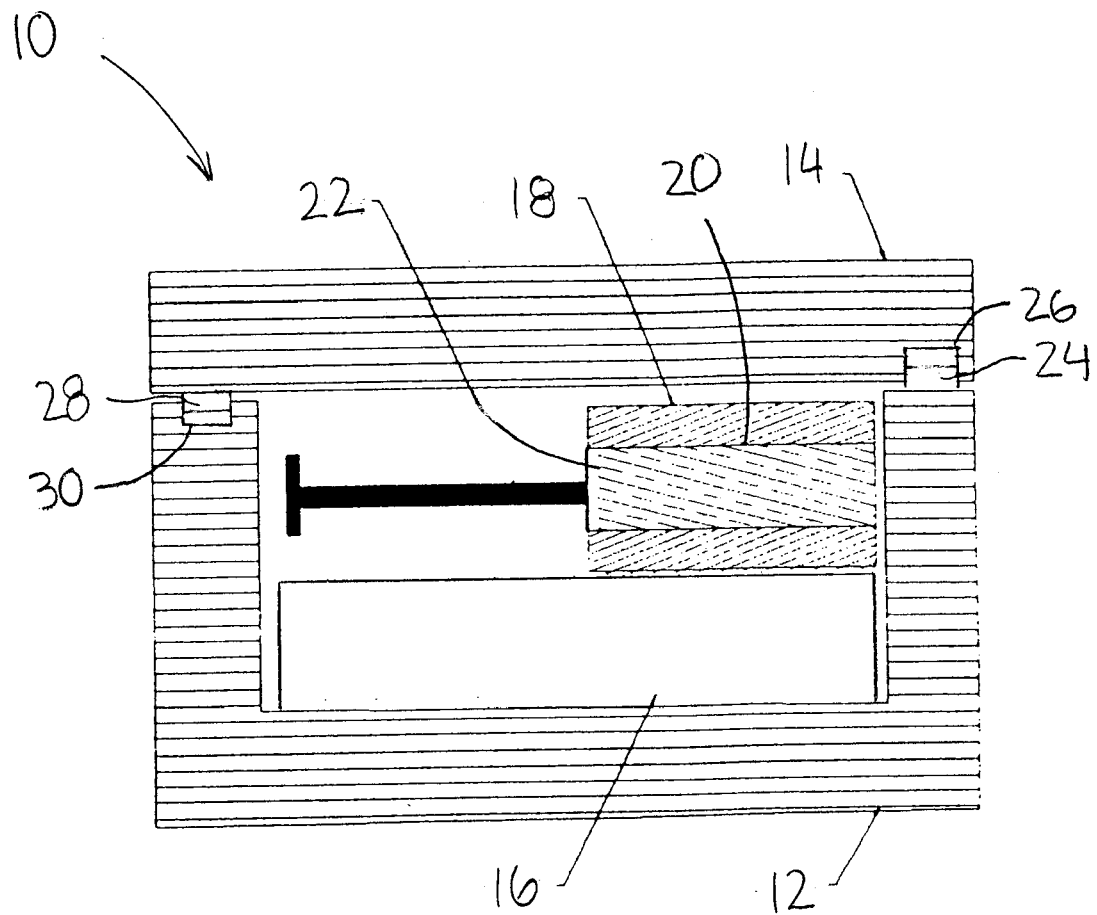
FIG. 1B is a side view of the disposable container of FIG. 1A.
Figure 2:
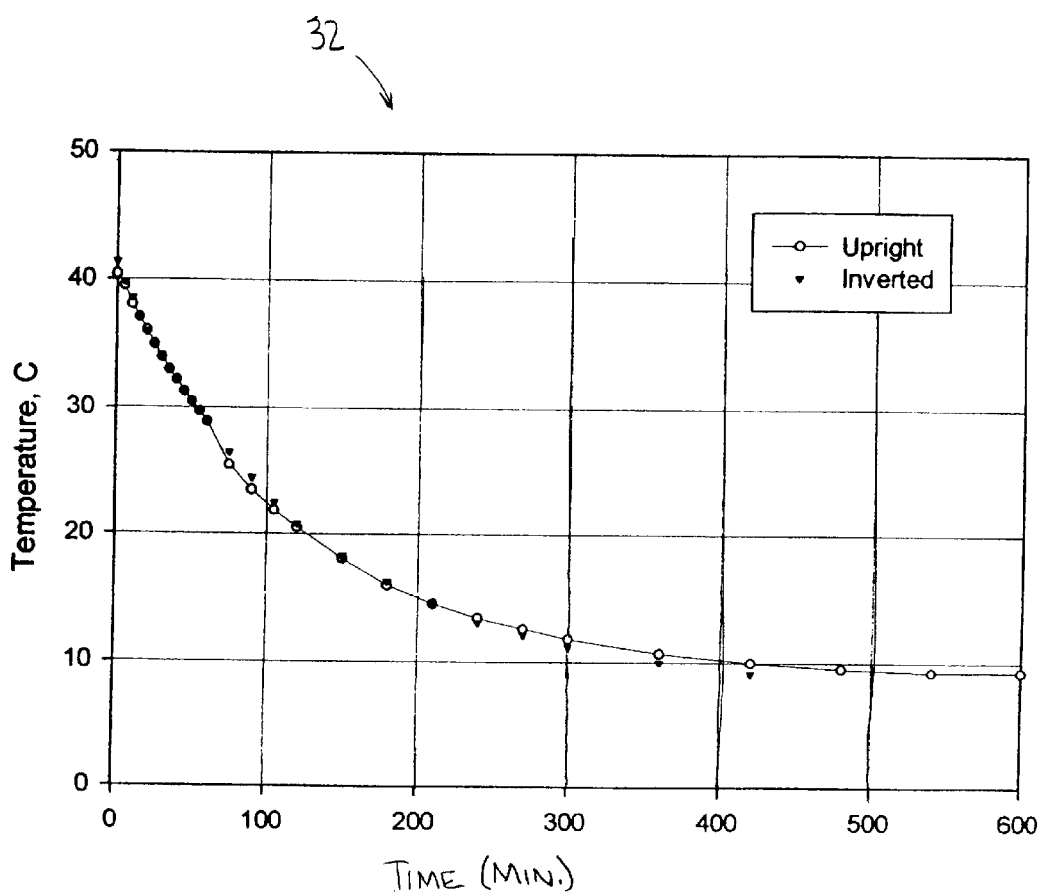
FIG. 2 is a chart plotting measured cooling rates for upright or inverted disposable containers, according to one aspect of the present invention.

An illustrative embodiment of the present invention relates to a disposable storage container that includes an insulating box. Inside the insulating box, a plastic foam insert is provided. The foam insert has a plurality of drilled holes or chambers provided therein for storing sample syringes or tubes. When an equine semen sample is to be transported, the sample is placed in the sample syringe or tube. A block of cooling material is also disposed within the disposable storage container to initiate cooling of the sample, and maintain a desired cooled temperature for a predetermined duration.

FIGS. 1A through 3, wherein like parts are designated by like reference numerals throughout, illustrate an example embodiment of a disposable storage container according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1A illustrates a front view of a disposable storage container 10 suitable for use in storing and transporting animal semen, especially equine semen. One of ordinary skill in the art will appreciate that the disposable storage container 10 can include a number of different variations.

The disposable storage container 10 is formed of an insulated box 12. The insulated box 12 has four walls and a floor that are insulated. The insulation can take the form of, for example, a foamed plastic, e.g., Styrofoam insulation. An insulated cover 14 fits on top of the insulating box 12, and can also be made of foamed plastic insulation. A friction fit between the insulated cover 14 and the insulated box 12 holds the insulated cover 14 in place. However, one of ordinary skill in the art will appreciate that an additional external fastening mechanism, such as a clasp or a circumferential band, can hold the insulated cover 14 on the insulated box 12, if desired. In addition, the insulated cover 14 can fit on the insulated box 12 using a tongue and groove configuration, or the like.

A cooling pack 16 is disposed inside the insulated box 12. The cooling pack 16 serves as the source for cooling the contents of the insulated box 12. The cooling pack 16 can include any number of known cooling sources, such as, for example, ice, mixtures of water with other materials, or other phase-change coolants known to one of ordinary skill in the art, and the like.

An insert 18 is disposed inside the insulated box 12 on top of, and in physical contact with, the cooling pack 16. The insert 18 can be made of such materials as plastic, foamed polyethylene, other foamed plastic, wood, and the like. The insert 18 can otherwise be referred to as an isothermalizer, which indicates that the insert 18 helps to regulate the temperature of its contents.

Although the materials of the insulated box 12, the insulated cover 14, and the insert 18 can vary, it should be noted that the relative cost of the materials is an important factor in determining which material to utilize, in addition to the relative heat transfer properties. A more expensive material will result in a more expensive storage container, which may prevent or make more difficult the characteristic of being disposable. As such, different variations to the materials utilized in manufacturing the storage container must take into consideration the relative cost, to ensure that the relative cost remains sufficiently low to maintain the disposability of the container.

The insert 18 includes a plurality of chambers 20 disposed within the insert 18. The chambers 20 are each sized and dimensioned to accommodate one or more storage capsules in the form of a syringe or tube 22, capable of holding a semen sample. The chambers 20 can be contained within the insert 18, or can pass through the insert 18, creating openings at two ends of the insert 18. There are two chambers 20 illustrated, in FIG. 1A, but one of ordinary skill will appreciate that there can be a different number of chambers, limited in part by the size of the chamber 20 and the size of the insert 18.

The syringe or tube 22 is suitable for containing and storing a desired amount of semen sample, such as equine semen, or thermal ballast, for an extended duration. The extended duration can be several days or more. Further, the syringe or tube 22 itself can be capable of storing the semen sample much longer, with the actual storage time being limited by the duration of the cooling effect provided by the cooling pack 16 on the semen sample. The syringe or tube 22 can be made of, for example, plastic, glass, composite, metal, and the like.

After preparation, the semen sample is diluted with extender, and the extended sample is placed into the sample containers in the form of the syringe or tube 22. These are normally two 50 ml syringes, although two 20 ml syringes and one 50 ml (thermal ballast) tube may be used in accordance with one embodiment of the present invention. The equivalent 50 ml and 20 ml Falcon-type centrifuge tubes may also be used to contain the samples. One of ordinary skill in the art will appreciate that the size and shape of the syringe can vary to include a number of different sizes and shapes. In addition, as described below, the relative quantities of semen sample and thermal ballast disposed in the syringes or tubes 22 can also vary, depending on the amount of semen sample desired to be stored and transported.

A user places the cooling pack 16 inside the insulated box 12 of the disposable storage container 10, on the bottom or floor of the insulated box 12. The user then loads the insert 18 on top of the cooling pack 16, in direct contact with the cooling pack 16. The level of contact must be sufficient to enable conductive heat transfer from the cooling pack 16 to the semen sample, or the semen sample and thermal ballast, inside the syringe or tube 22.

To close the insulated box 12 and seal the interior, the user places the insulated cover 14 of the insulated box 12 on top of the insert 18. The insulated cover 14 limits movement of the insert 18, by frictionally holding the insert 18 in place. The disposable storage container 10 is thus closed and sealed in preparation for extended storage and/or transportation.

The disposable storage container 10 uses the conductive flow of heat through the insert 18 to provide a required rate of cooling in the sample. In accordance with one embodiment, the dimensions of the syringe or tube 22, insert 18, and cooling pack 16 are carefully designed and tested so that the required cooling rate of 0.1°/minute is obtained at a temperature of 20°. The disposable storage container 10 does not rely on convective cooling to cool the semen sample; the disposable storage container 10 relies on conductive cooling. The reliance upon conductive cooling translates to an insensitivity toward orientation of the disposable storage container 10. The disposable storage container 10 may be turned upside-down, sideways, right-side-up, or in any other orientation during transportation, and there will be a negligible effect on the cooling rate and the final temperature inside the disposable storage container 10 at the location of the semen sample.

An example disposable storage container 10 was constructed. In the example embodiment, the sample volume was set to 100 ml. The materials were then selected to achieve an appropriate cooling rate and final temperature for the 100 ml semen sample. The insert 18 was constructed of polyethylene foam (weight 1.5 lb/cu ft). The insert 18 was about 2.0 inches thick, with a width of 4 inches and a length of 5 inches. The chambers 20 disposed in the insert 18 were arranged so that the body of the syringe or tube 22 fit snugly into the space of the chamber 20 with a friction fit. The conductivity of the foam is sufficient to provide the correct required or optimum cooling rate of 0.10±0.03° C./minute at 20° C., as well as the final temperature in the required range 5° C.–9° C., according to the desired parameters for this example.

The insulated box 12 of the disposable storage container 10 has an internal shape designed such that the coolant pack 16 fits on the base of the insulated box 12 without significant movement sideways. The walls of the insulated box 12 have a shape such that the insert 18 stays in place laterally, but can still slide down vertically into the insulated box 12 to make contact with the cooling pack 16. The insulated box cover 14 keeps slight positive pressure on the top of the insert 18, which in turn rests on the cooling pack 16. Thus, all of the components are held in place.

The entire disposable storage container 10 fits into a cardboard box (not shown) for transportation. The cardboard box serves to hold the insulated cover 14 of the insulated box 12 firmly in place when in a closed position. To prevent ambiguity in the correct positioning of the insulated cover 14 on the insulated box 12, the top of the insulated box 12 has a projecting box ridge 24, which fits into a cover slot 26 in the insulated cover 14 (tongue and groove). On the opposite side of the insulated box 12, the situation is reversed. A cover ridge 28 on the insulated cover 14 fits into a box groove 30 on the top of the insulated box 12. In this way, the insulated cover 14 can only be placed on the insulated box 12 in one orientation, which locks the insulated cover 14 into place, and ensures that all of the components are properly held in place within the insulated box 12.

Experiments were performed on the disposable storage container 10 constructed in accordance with this disclosure to determine a rate of cooling within the disposable storage container 10 at about 20° C. One parameter of the experiment was that a cooling rate of about 0.1° C./min at 20° C. should be obtained. A second parameter of the experiment was that a total of 100±10 ml of semen sample plus thermal ballast (if necessary) should be in the syringes or tubes 22. In the example embodiment constructed, the insert 18 was designed such that the cooling rate for this volume of sample would achieve the desired 0.1° C./min at about 20° C.

The thermal ballast is placed in the insert 18, adjacent the semen sample or samples, to provide a predetermined thermal inertia that must be cooled by the cooling pack 16. The dimensions, locations, and materials of each of the components making up the disposable storage container 10 are designed to work with a selected thermal inertia total. If the quantity of the semen sample is less than that required for the selected thermal inertia, the thermal ballast is added to the insert to achieve the required thermal inertia. Further details concerning the application of the thermal ballast can be found in U.S. Pat. No. 4,530,816, which is hereby incorporated by reference herein.

It should be noted that for lower amounts of semen samples, substantially the same thermal behavior is obtained if a ballast tube containing water, initially at substantially the same temperature as the semen sample, is placed in the insert 18. Thus, for two 20 ml semen samples, an additional ballast tube containing 50 ml of water would be added to insert 18. A ballast tube is simply a storage capsule in the form of the syringe or tube 22, filled with something other than a semen sample, such as water. The amount of thermal ballast will vary to accommodate the desired total amount of sample and ballast required for the particular storage container configuration. The ballast tube creates additional thermal energy to be transferred to the cooling pack 16, such that the overall thermal burden placed on the cooling pack 16 is within design parameters for the particular container configuration and cooling pack 16 size.

It should also be noted that for different amounts of semen samples and/or thermal ballast, one of ordinary skill in the art will appreciate that different sizes of the components of the disposable storage container 10 will be required. More specifically, a disposable storage container suitable for storing and transporting an amount of semen sample and/or thermal ballast greater than about 100 ml to 120 ml, will require a thinner insert. In this way, the same cooling rate for the larger thermal mass of extended-semen-plus-ballast is obtained, by reducing the thermal resistance of the insert. Contrarily, a disposable storage container suitable for storing and transporting an amount of semen sample and/or thermal ballast less than about 80 mil to 100 ml, will require an insert having higher thermal impedance. The specific dimensions provided herein are based on a given parameter of 100 ml of semen sample or semen sample and thermal ballast in total.

A sample temperature was measured using a calibrated electric thermistor, located inside one of two 50 ml tubes 22. The tubes 22 were initially loaded with water at about 40° C., and then loaded into the insert 18. The insert 18 was then loaded into the insulated box 12 on top of the cooling pack 16. The temperature measurements were plotted to create a cooling curve representing the starting temperature, ending temperature, and rate of cooling.

The design of the example embodiment disposable storage container 10 was tested in practice by measuring the exact cooling curves of samples loaded into the insert 18, when the disposable storage container 10 was placed in two different orientations. In a first orientation, the disposable storage container 10 was positioned upright. In a second orientation, the disposable storage container 10 was positioned inverted or upside-down. The cooling rates, illustrated by cooling curves shown in a plot 32 in FIG. 2, were then compared. The resultant experimental cooling curve obtained with the example disposable container 10 being upright (labeled "Upright" in the figure) has a substantially identical slope to the resultant experimental cooling curve obtained with the example disposable container 10 being inverted (labeled "Inverted" in the figure). More specifically, the curves between 37° C. and 10° C. are indistinguishable. Both indicate a cooling rate close to 0.1° C. at a temperature of about 20° C. This indicates that the cooling rate for the sample in the upright position was substantially identical to the cooling rate for the sample in the upside-down position.

The use of the insert 18 enables a cooling rate independent of orientation. Inversion of the unit provides a cooling curve, which is indistinguishable from that for the upright unit over the critical transition near 20° C., as would be expected. The insert 18, therefore, allows a properly controlled thermal regime for the sample during transportation.

It should be noted that the sample syringes or tubes 22 are in a thermal gradient, which is normal to the tube axis. A characteristic of the insert 18 is that the sample syringe or tube 22 rapidly becomes adequately isothermal, as its cooling proceeds. A mathematical model of the sample syringe or tube 22 in the insert 18 is shown in a plot 34 in FIG. 3. The external temperature is taken as 22° C. in the calculation, and the temperature of the cooling pack 16 as taken as 0° C. Finite element analysis has been used to solve the time-dependent thermal conduction differential equation.

Figure 3:
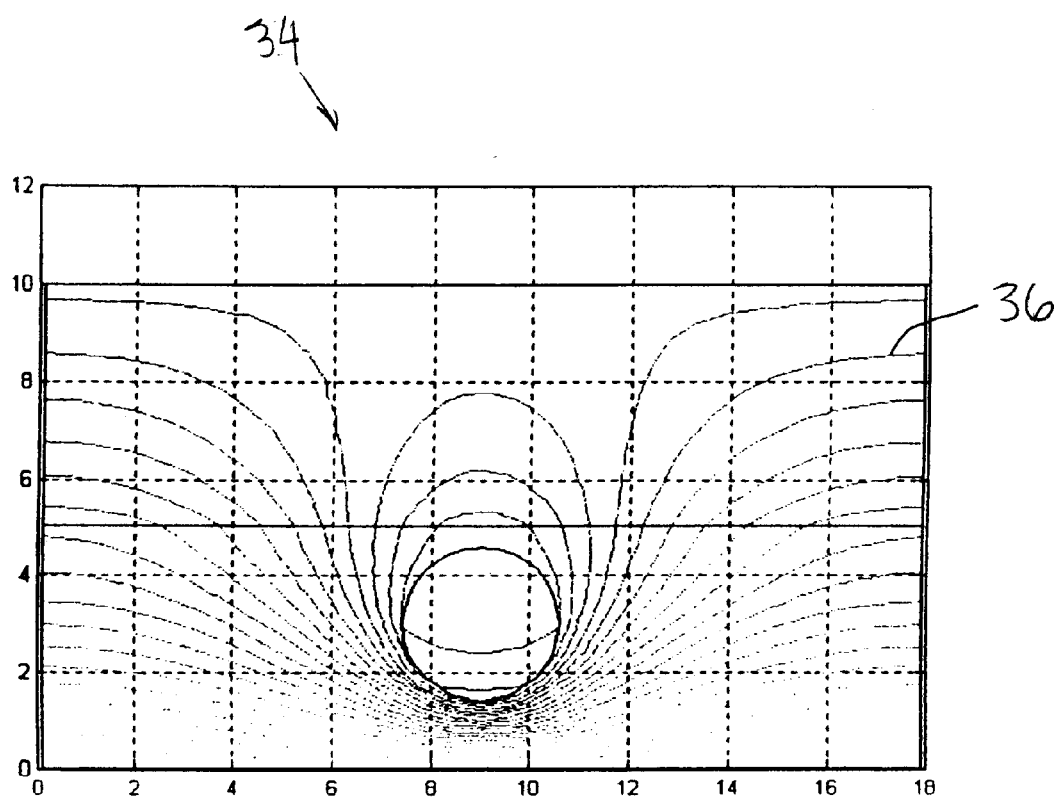
FIG. 3 is a graphic illustration of a mathematical model of a sample tube stored in the disposable container, according to one aspect of the present invention.

In FIG. 3, isotherms 36 are shown for a time 105 minutes after loading the disposable storage container 10 with the sample, corresponding to a sample temperature near 22° C. The heat equation, as understood by one of ordinary skill in the art, is solved using the appropriate thermal conductivity for the polyethylene foam and for the (mainly aqueous) sample in this example. It should be noted that in the geometry chosen, with cooling in a direction perpendicular to the sample syringe or tube 22 axis, the sample itself remains almost isothermal across the syringe or tube 22 during the cooling process, despite the high thermal gradient in the insert 18. This is due to the relatively high thermal conductivity of the sample.

The exemplified geometry for the insert 18 and for sample cooling sufficiently maintains a uniform temperature in the semen sample. The cooling rate for the semen sample is close to the ideal value for equine semen, as well as giving a final temperature between about 5° C. and 9° C.

One of ordinary skill in the art will appreciate that the present disclosure includes example embodiments for implementing the invention for the storage and transportation of equine semen. The temperature ranges provided for final temperatures and for cooling rates are representative of what is currently known to be optimal for the storage and transportation of equine semen. However, it is understood that additional experimentation may reveal different optimal temperature ranges and rates of cooling. The present invention can be modified to accommodate such different temperatures and rates of cooling, by modifying the dimensions and materials of the insulated box, the cooling pack, the insert, and the insulated cover. In addition, the characteristics of the resulting disposable storage container can be altered to accommodate optimal temperature ranges and rates of cooling for non-equine semen, such as for canine, bovine, or other semen that may require storage and transportation.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

What is claimed is:

1. A storage and transportation container for storing and transporting a semen sample, comprising:

an insulated box having at least a first portion being a box protruding ridge, at least a second portion being a box recessed groove, and a floor;

an insulated cover having at least a first portion having a cover recessed groove and being located to receive the box protruding ridge only when the insulated cover is placed on the insulated box in a predetermined orientation, and the insulated cover having at least a second portion having a cover protruding ridge and being located to be received into the box recessed groove only when the insulated cover is placed on the insulated box in the predetermined orientation;

a cooling pack disposed on the floor of the insulated box; and an insert disposed to rest on the cooling pack inside the insulated box, such that the cooling pack is beneath the insert when the insulated box is in an upright position, the insert having at least one chamber for receiving a storage capsule holding at least the semen sample;

wherein the insulated cover frictionally fits on the insulated box and makes contact with the insert to hold the insert in place, and wherein the insert makes sufficient contact with the cooling pack to enable conductive cooling of the semen sample in the insert.

2. The storage and transportation container of claim 1, wherein the insulated box is formed of foam plastic.

3. The storage and transportation container of claim 1, wherein the insulated cover is formed of foam plastic.

4. The storage and transportation container of claim 1, wherein the insert is formed of foam plastic.

5. The storage and transportation container of claim 1, wherein the at least one chamber is sized and dimensioned to hold a storage capsule suitable for holding at least the semen sample.

6. The storage and transportation container of claim 5, wherein the semen sample comprises equine semen.

7. The storage and transportation container of claim 5, wherein the storage capsule is at least one of a syringe and a tube.

8. The storage and transportation container of claim 5, wherein the storage capsule is sized and dimensioned to hold about 50 ml of at least the semen sample.

9. The storage and transportation container of claim 5, wherein the storage capsule is sized and dimensioned to hold about 20 ml of at least the semen sample.

10. The storage and transportation container of claim 1, wherein there are a plurality of chambers in the insert.

11. The storage and transportation container of claim 1, further comprising a second storage capsule holding a thermal ballast material.

12. The storage and transportation container of claim 11, wherein a sum of the capacity of the semen sample and the thermal ballast material able to be stored in the at least one chamber is about 90 ml to about 110 ml.

13. The storage and transportation container of claim 1, wherein a sum of the capacity of the semen sample able to be stored in the at least one chamber is about 90 ml to about 110 ml.

14. The storage and transportation container of claim 11, wherein a sum of the capacity of the semen sample and the thermal ballast material able to be stored in the at least one chamber is about 80 ml to about 120 ml.

15. The storage and transportation container of claim 1, wherein a sum of the capacity of the semen sample able to be stored in the at least one chamber is about 80 ml to about 120 ml.

16. The storage and transportation container of claim 1, wherein a cooling rate of the semen sample in the insert is about 0.1° C./min at about 20° C.

17. The storage and transportation container of claim 11, wherein a cooling rate of the semen sample and the thermal ballast material in the insert is about 0.1° C./min at about 20° C.

18. A method of packing a semen sample for storage or transportation, comprising:
providing an insulated box having a floor;
placing a cooling pack on the floor of the insulated box;
placing an insert on top of and in contact with the cooling pack, the insert having at least one storage capsule holding the semen sample disposed within at least one chamber of the insert;
placing an insulated cover on top of and substantially in contact with the insert, the insulated cover having a friction fit with the insulated box.

19. The method of claim 18, wherein an insulated cover has at least a first portion having a cover recessed groove located to receive a box protruding ridge to form the friction fit only when the insulated cover is placed on the insulated box in a predetermined orientation, and the insulated cover has at least a second portion having a cover protruding ridge located to be received into a box recessed groove to form the friction fit only when the insulated cover is placed on the insulated box in the predetermined orientation.

20. The method of claim 18, wherein at least one of the insulated box, the insulated cover, and the insert, is formed of foam plastic.

21. The method of claim 18, wherein the semen sample comprises equine semen.

22. The method of claim 18, wherein the storage capsule is at least one of a syringe and a tube.

23. The method of claim 18, wherein the storage capsule is sized and dimensioned to hold about 50 ml of the semen sample.

24. The method of claim 18, wherein the storage capsule is sized and dimensioned to hold about 20 ml of the semen sample.

25. The method of claim 18, wherein there are a plurality of chambers in the insert.

26. The method of claim 18, wherein a sum of the capacity of the semen sample able to be stored in the at least one chamber is about 90 ml to about 110 ml.

27. The method of claim 18, wherein a sum of the capacity of the semen sample able to be stored in the at least one chamber is about 80 ml to about 120 ml.

28. The method of claim 18, wherein a cooling rate of the semen sample in the insert is about 0.1° C./min at about 20° C.

29. The method of claim 18, further comprising a second storage capsule holding a thermal ballast material.

30. The method of claim 29, wherein a sum of the capacity of the semen sample and the thermal ballast material able to be stored in the at least one chamber is about 90 ml to about 110 ml.

31. The method of claim 29, wherein a sum of the capacity of the semen sample and the thermal ballast material able to be stored in the at least one chamber is about 80 ml to about 120 ml.

32. The method of claim 29, wherein a cooling rate of the semen sample and the thermal ballast material in the insert is about 0.1° C./min at about 20° C.

* * * * *